United States Patent [19]
Gilli et al.

[11] Patent Number: 5,191,884
[45] Date of Patent: Mar. 9, 1993

[54] RECONFIRMATION PRIOR TO SHOCK FOR IMPLANTABLE DEFIBRILLATION

[75] Inventors: Norma L. Gilli, Mosman; Lorraine Holley, Rockdale; Geoffrey A. Drane, Annandale; Anthony C. Stephens, Willoughby; Christopher N. Daly, Bilgola Plateau, all of Australia; Steven M. Maas, Englewood, Colo.

[73] Assignee: Telectronics N.V., Curacao, Netherlands Antilles

[21] Appl. No.: 576,178

[22] Filed: Aug. 29, 1990

Related U.S. Application Data

[63] Continuation of Ser. No. 239,624, Sep. 1, 1988, abandoned.

[30] Foreign Application Priority Data

Sep. 2, 1987 [AU] Australia .................. PI4104

[51] Int. Cl.$^5$ .............................................. A61N 1/39
[52] U.S. Cl. ............................................... 128/419 D
[58] Field of Search ........ 128/419 PG, 419 D, 419 P, 128/705

[56] References Cited

U.S. PATENT DOCUMENTS

| | | | |
|---|---|---|---|
| Re. 30,372 | 8/1980 | Mirowski et al. | 128/419 D |
| 3,703,900 | 11/1972 | Holznagel | 128/419 P |
| 3,716,059 | 2/1973 | Welborn et al. | 128/419 D |
| 3,805,795 | 4/1974 | Denniston et al. | 128/419 D |
| 3,942,534 | 3/1976 | Allen et al. | 128/419 PG |
| 4,181,133 | 1/1980 | Kolenik et al. | 128/419 PG |
| 4,280,502 | 7/1981 | Baker, Jr. et al. | 128/419 PG |
| 4,307,725 | 12/1981 | Sowton et al. | 128/419 PG |
| 4,375,817 | 3/1983 | Engle et al. | 128/419 D |
| 4,427,011 | 1/1984 | Spurrell et al. | 128/419 D |
| 4,440,172 | 4/1984 | Langer | 128/419 D |
| 4,473,078 | 9/1984 | Angel | 128/419 PG |
| 4,572,191 | 2/1986 | Mirowski et al. | 128/419 D |
| 4,610,254 | 9/1986 | Morgan et al. | 128/419 D |
| 4,774,950 | 10/1988 | Cohen | 128/419 D |
| 4,787,389 | 11/1988 | Tarjan | 128/419 PG |
| 4,830,006 | 5/1989 | Haluska et al. | 128/419 PG |
| 4,872,459 | 10/1989 | Pless et al. | 128/419 PG |

FOREIGN PATENT DOCUMENTS

| | | |
|---|---|---|
| 0009255 | 4/1980 | European Pat. Off. . |
| 0038080 | 10/1981 | European Pat. Off. . |
| 8202836 | 9/1982 | PCT Int'l Appl. ............. 128/419 D |

OTHER PUBLICATIONS

Stephens et al., "The Automatic Detection of Ventricular Tachyarrhythmias and Reconfirmation During Defibrillator Charge Sequences in Dogs"; Abstract No. 122, PACE, vol. 10, Jul.-Aug., 1987, Part II, p. 999.

Primary Examiner—William E. Kamm
Assistant Examiner—Kennedy J. Schaetzle
Attorney, Agent, or Firm—Gottlieb, Rackman & Reisman

[57] ABSTRACT

A multiprogrammable, telemetric, implantable defibrillator contains a high energy shock system to revert VT/VF's to normal sinus rhythm and a multi-programmable VVI bradycardia support system. When the apparatus is in an automatic shock sequence, there are two points of reconfirmation: at the programmed minimum time to shock and after the full charge has been reached, or at thirty seconds, whichever comes first. Reconfirmation involves testing the tachycardia detection output (TDO). If the TDO is high, reconfirmation occurs. If the TDO is low, reconfirmation will not occur and the device will subsequently dump the discharge. Two reconfirmations must occur before a shock is delivered to the patient. If the TDO is low at either reconfirmation, the charge will be dumped.

14 Claims, 16 Drawing Sheets

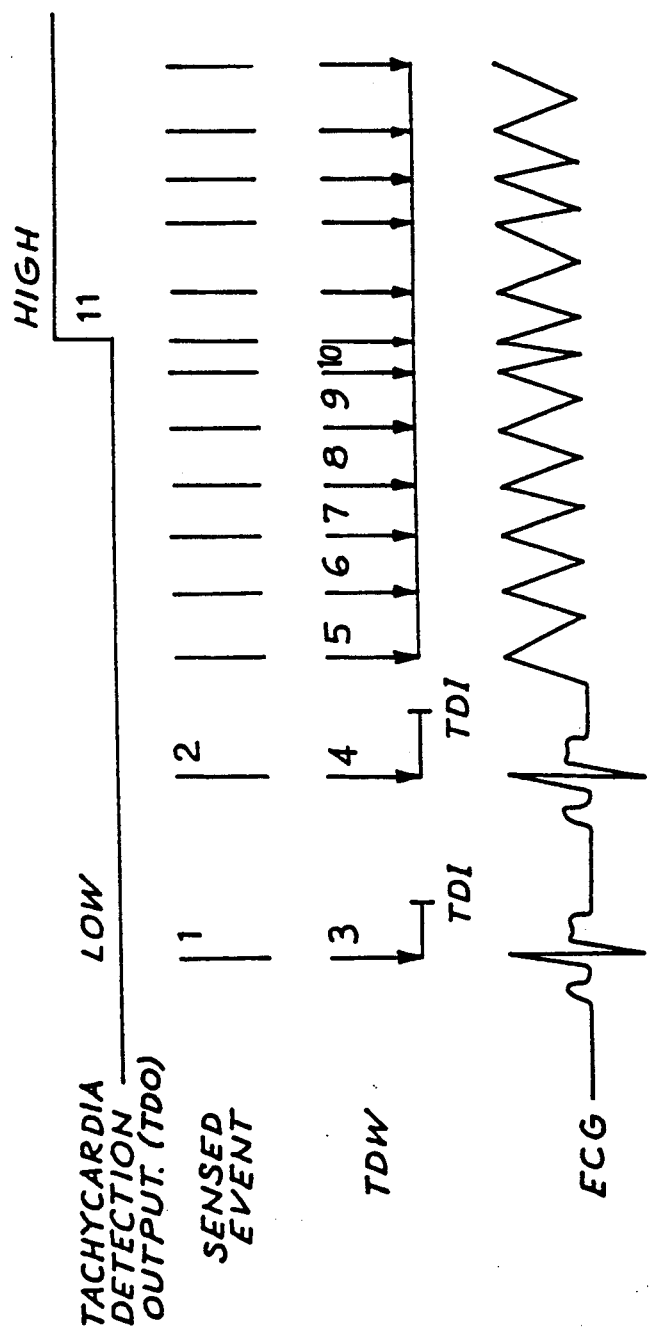

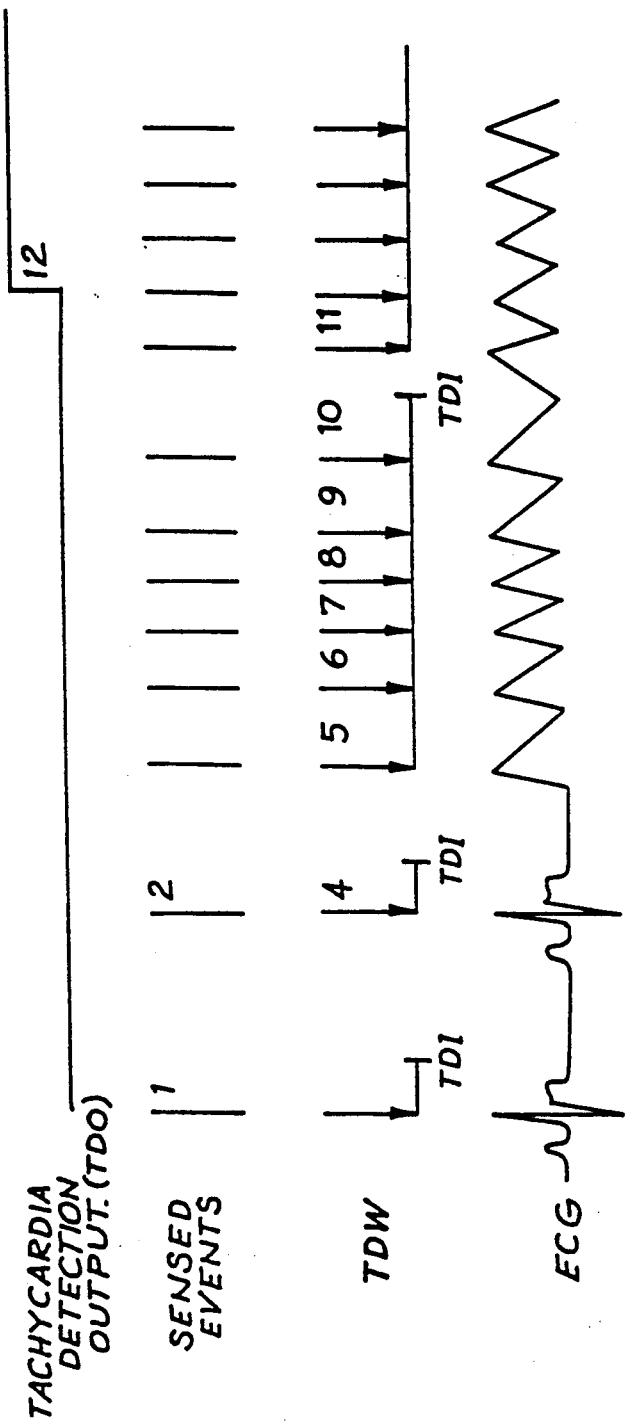
FIG. 4A VT/VF DETECTION ALGORITHM: A MISSED INTERVAL

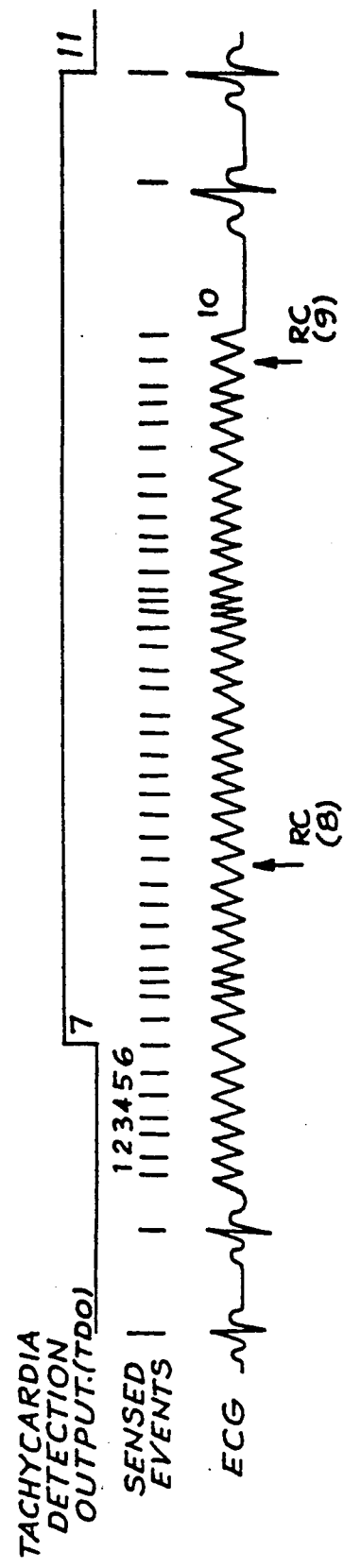
FIG. 5  INITIAL SHOCK SEQUENCE

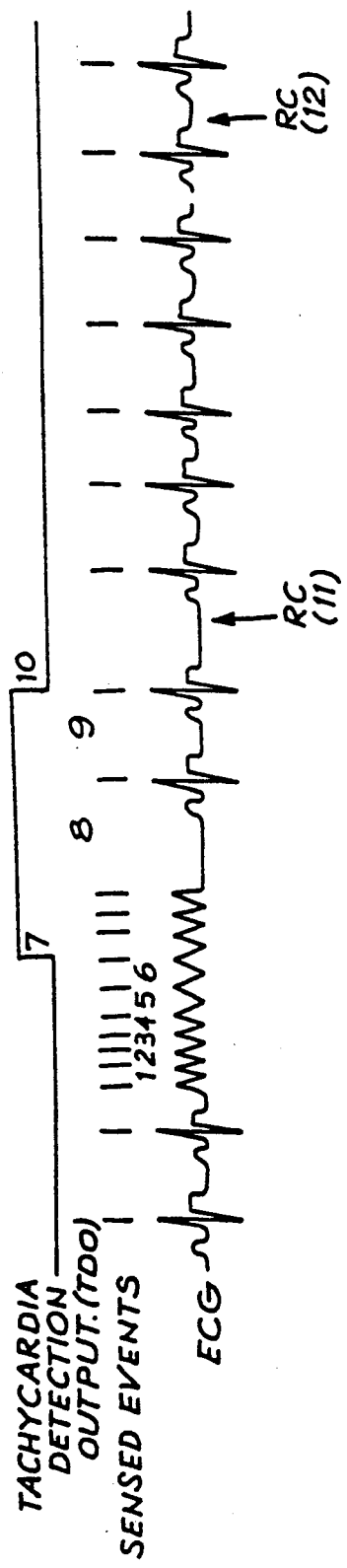
FIG. 5A SPONTANEOUS REVERSION BEFORE FIRST RECONFIRMATION

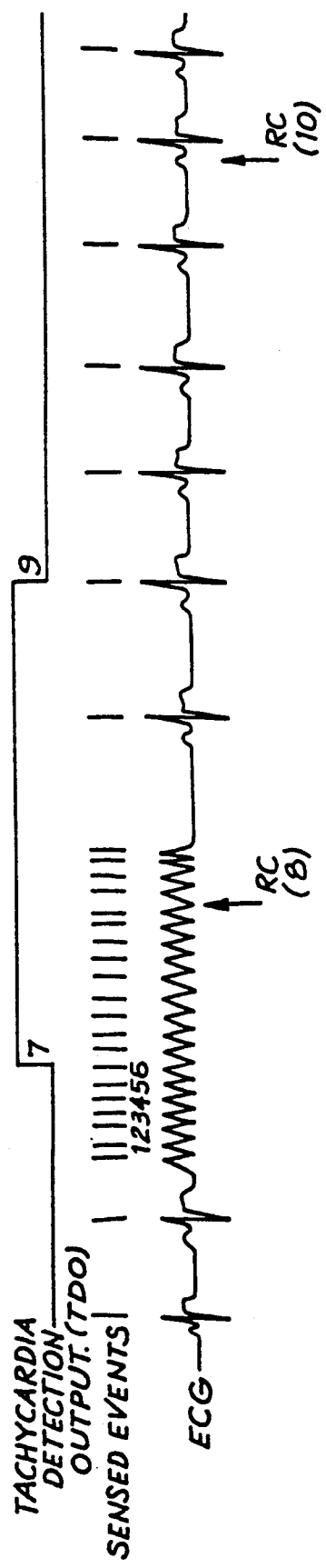
FIG. 5B  SPONTANEOUS REVERSION BEFORE SECOND RECONFIRMATION

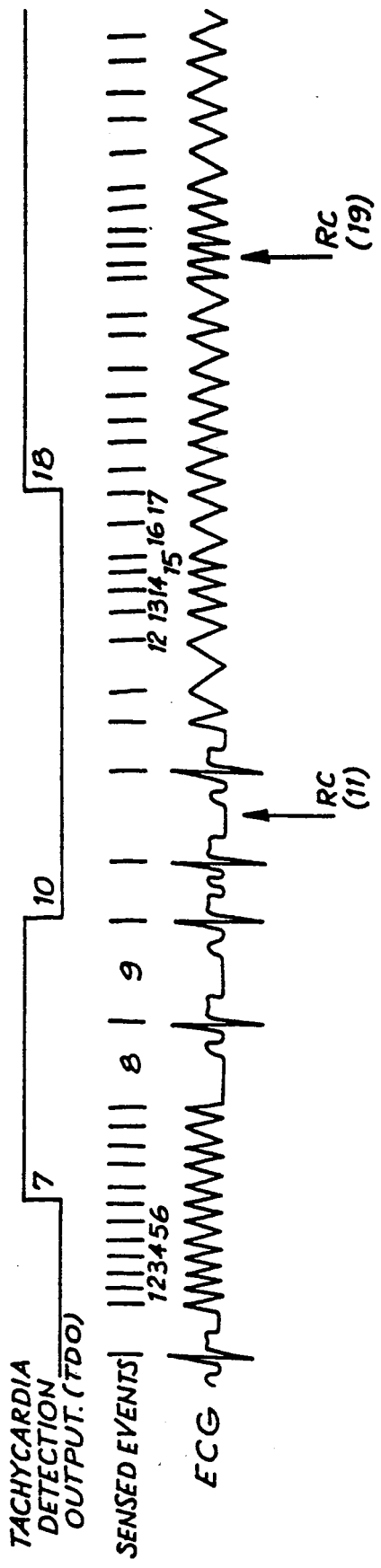
FIG. 5C SPONTANEOUS REVERSION AND REDETECTION

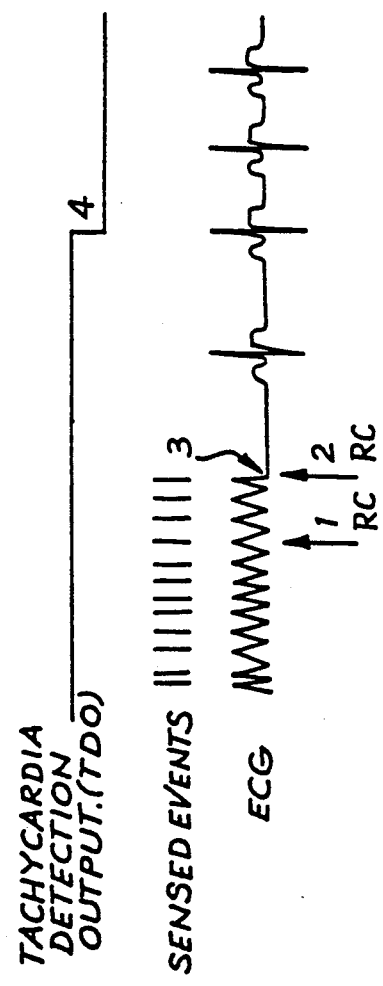
FIG. 6 SUBSEQUENT SHOCK SEQUENCE

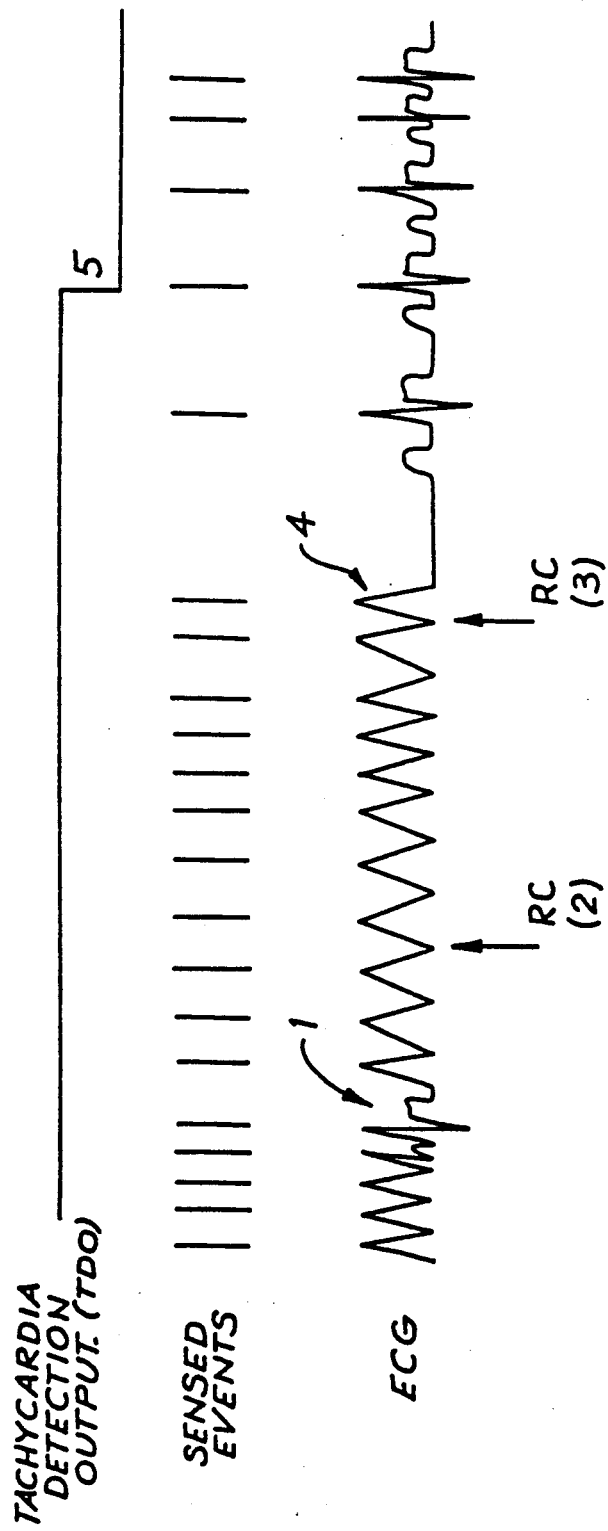
FIG. 6A CHARGE SEQUENCE AFTER A FAILED SHOCK

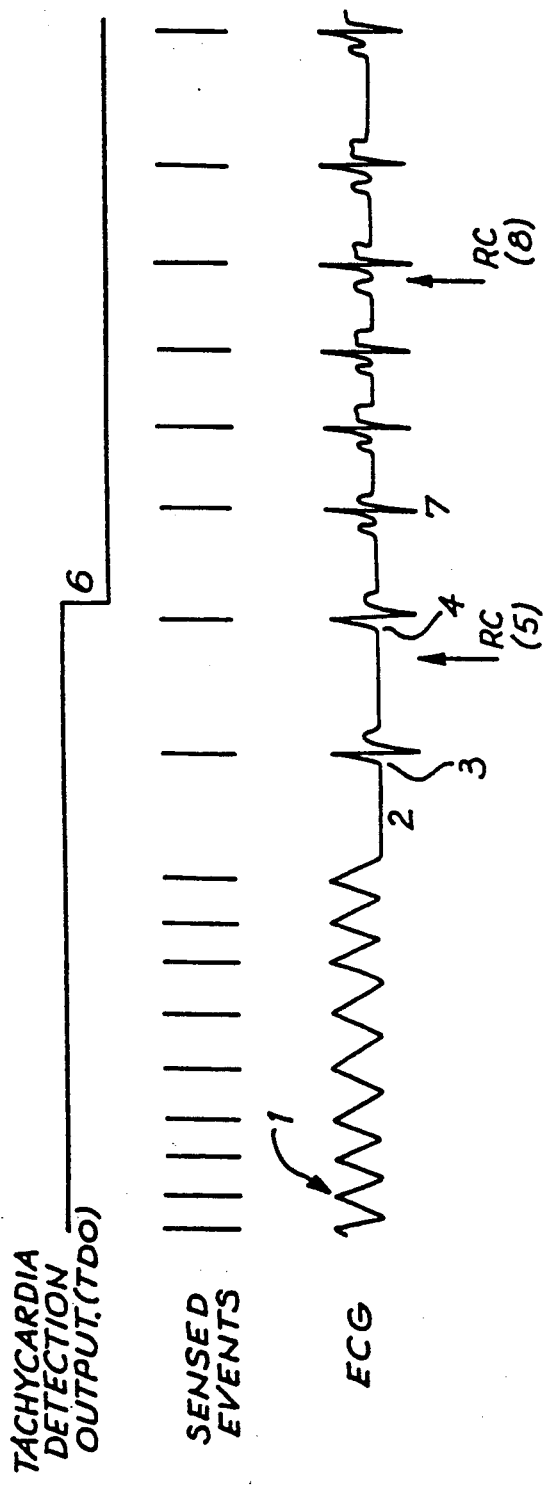
FIG. 6B SPONTANEOUS REVERSION FOLLOWING A SHOCK

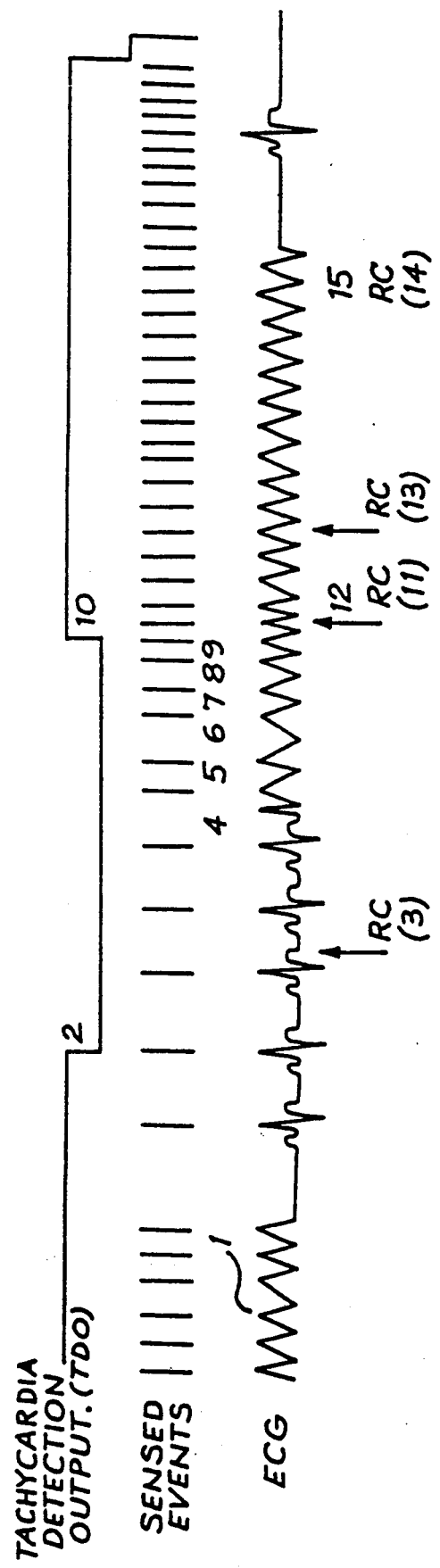

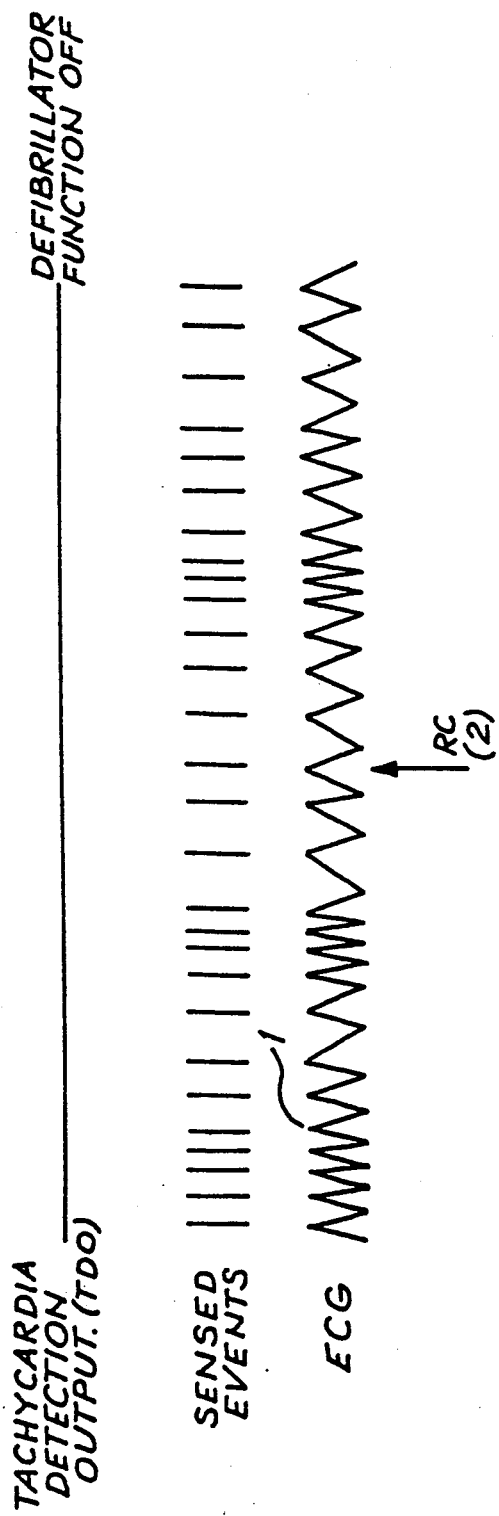
FIG. 7 RECONFIRMATION AFTER LAST SHOCK

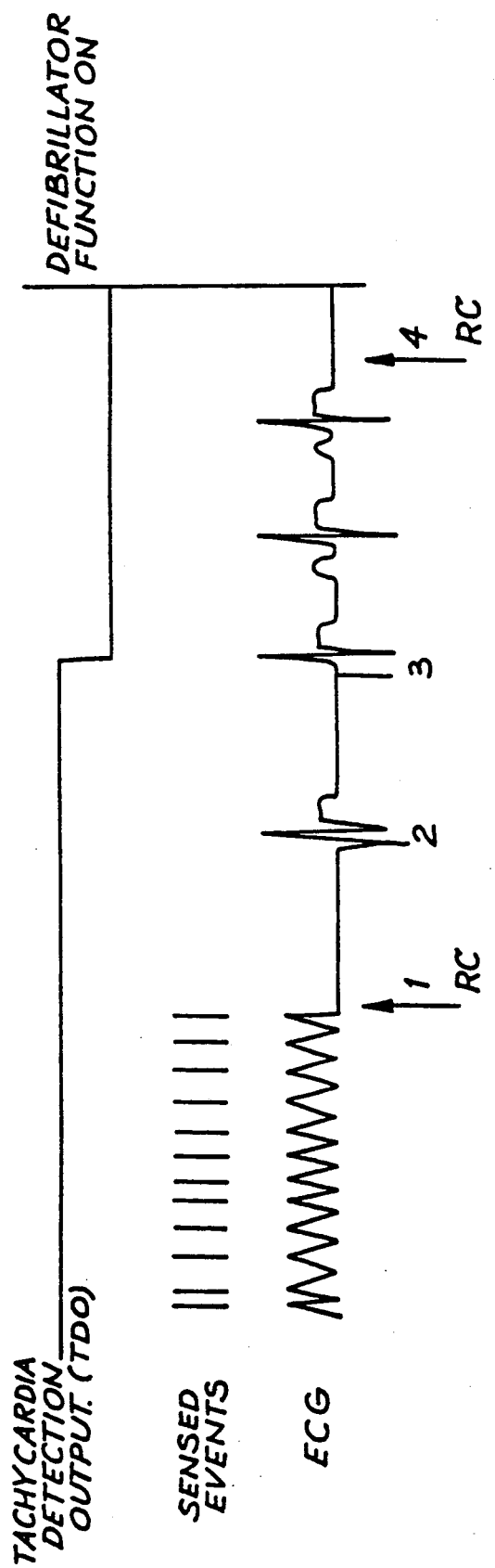
FIG. 7A LAST SHOCK IN A SERIES – LAST SHOCK SUCCESSFUL

RECONFIRMATION PRIOR TO SHOCK FOR IMPLANTABLE DEFIBRILLATION

This is a continuation of application Ser. No. 07/239,624, filed Sep. 1, 1988, now abandoned.

FIELD OF THE INVENTION

This invention relates to multi-programmable telemetric implantable cardioverters and defibrillators, and in particular to a cardioverter or defibrillator with a shock system for reverting ventricular tachycardia (VT) or ventricular fibrillation (VF) to normal sinus rhythm (NSR) in addition to performing multi-programmable bradycardia pacing support as well as to a method for reverting VT or VF to NSR.

PRIOR ART

U.S. Pat. No. 3,857,398 to Rubin describes a combined pacer/defibrillator. This apparatus either performs a pacing function or a defibrillation function depending on whether a VT/VF is detected. If a VT/VF is detected, the apparatus is switched to the defibrillating mode. After a period of time to charge the capacitor, a defibrillation shock is delivered to the patient. A problem with this type of apparatus is that it does not allow for a spontaneous reversion of the VT/VF between detection and shock. For example, if the VT/VF spontaneously reverts after initial detection of the VT/VF and prior to shocking, the patient is unnecessarily given a defibrillation shock. This can be a very traumatic experience to a patient when given unnecessarily and may initiate a new arrhythmia. It is highly desirable therefore from the viewpoint of patient safety to prevent unnecessary defibrillation shocks.

In general non-sustained VT, atrial flutter, atrial fibrillation or supraventricular tachycardia all may result in unnecessary shocks being delivered to the patient. An additional problem exists at times with an apparatus appearing to detect an arrhythmia when it may be caused by electromagnetic interference (EMI). Again, it is possible that an unwanted discharge may be given to the patient.

A defibrillator apparatus is disclosed in U.S. Pat. No. Re. 27,652 of Mirowski et al. (based on original U.S. Pat. No. 3,614,954) and U.S. Pat. No. Re. 27,757 of Mirowski et al. (based on original U.S. Pat. No. 3,614,955). This apparatus is referred to in the publication "Management of Cardiac Arrhythmias: The Non-Pharmacological Approach" by Edward V. Platla (published by J. B. Lippincott & Company, N.Y. 1987). At page 229 under the heading "Unwanted discharges", the article states that "Delivery of shocks during rhythms other than sustained ventricular tachyarrhythmias may occur. Rapid sinus tachycardia and other supra-ventricular rhythms that satisfy the sensing algorithm of the apparatus may result in unwanted discharges . . . . Shocks delivered during sinus rhythm can also be caused by non-sustained ventricular tachycardia. Although the sensing function in these instances is entirely appropriate, once the diagnosis is made and the capacitor charging cycle is initiated, the apparatus is committed to discharge, even if sinus rhythm has been restored in the interim. . . "

With reference to these unwanted shocks, the article then states in the next paragraph that ". . . they are clearly undesirable and every effort should be made to minimize their occurrence".

SUMMARY OF THE INVENTION

It is an object of the invention to increase patient safety in an implantable countershock apparatus.

It is a further object of the invention to prevent unnecessary shocks to a patient after an initial detection of a VT/VF.

It is a still further object of the invention to provide at least one reconfirmation of a VT/VF after its initial detection and prior to the time for delivering a shock to a patient, so that if a VT/VF is reverted following the initial detection, a shock is not delivered to the patient.

According to the invention, there is provided an apparatus for reverting ventricular tachycardia or ventricular fibrillation including means for detecting VT/VF and for delivering a countershock. The apparatus includes a means for reconfirmation of a detected VT/VF prior to the delivery of a shock. The apparatus also includes means for preventing delivery of a shock if the detected VT/VF is not reconfirmed. This means causes a dump discharge internally within the apparatus.

The invention further provides an apparatus for treating tachyarrhythmias comprising a tachyarrhythmia detecting means having a VT/VF detection algorithm. The apparatus includes a high energy shock system for delivering a defibrillation shock. The high energy shock system means includes means for discharging the stored energy either to a patient or dumping it internally within the apparatus. The apparatus further comprises a means for reconfirming a tachyarrhythmia at least once following detection and prior to the time for shock delivery. If there is no reconfirmation, the apparatus discharges the stored energy internally. If there is a positive reconfirmation, a shock is delivered to the patient at a predetermined time or when the desired energy level is reached. Preferably the apparatus is programmed to an automatic shock sequence.

Preferably, in accordance with the apparatus or method of the invention, there are two points of reconfirmation. The first reconfirmation point is at the programmed minimum time to shock. The second reconfirmation point is just after the full charge has been reached or at thirty seconds after the start of the shock sequence, whichever is first. At each reconfirmation point the tachycardia detection output (TDO) is tested. If the TDO is high, there is a positive reconfirmation. If the TDO is low, there is no reconfirmation and the charge is dumped. Thus, if the TDO is low at either reconfirmation point, the shock is dumped internally into the apparatus.

When a VT/VF is initially detected, the high energy shock system starts to charge to the programmed initial energy. The minimum time to shock may be a programmable parameter or a fixed period of time.

In one embodiment, if there is no reconfirmation at either of the two reconfirmation points, the charge is "flagged" for a dump discharge. As a preferred alternative, if there is no reconfirmation at the minimum time to shock (or at the first reconfirmation point), the apparatus may dump the discharge at that point and then go back to the defib standby condition for redetection. This provides an energy saving by preventing a full charge when the discharge is be dumped. It also provides a faster turn around for redetection should it be required.

The pacemaker of the apparatus is preferably a programmable VVI bradycardia support pacemaker, although a dual chamber pacemaker may be used. The apparatus therefore provides bradycardia back-up pacing in the event of a patient experiencing a spontaneous reversion from a VT/VF to an asystole condition or a bradycardia condition, thereby minimizing the time a patient is without an adequate heart rate.

The reconfirmation points as described in the preferred embodiment are two in number. However, there may be only one reconfirmation point or even three or more. The number of reconfirmation points and the time at which they occur may be programmable parameters. As an example, the time to a reconfirmation point for detected ventricular tachycardias may be a function of the haemodynamic state of the patient, particularly the tachycardia cycle length. Thus, for a fast VT there is a short tachycardia cycle length which may necessitate a faster reconfirmation. This is beneficial to patient safety in that it leads directly to the reduction of haemodynamic danger.

BRIEF DESCRIPTION OF THE DRAWINGS

Further objects, features and advantages of the invention will become apparent upon consideration of the following detailed description in connection with the accompanying drawings in which:

FIG. 4 illustrates the operation of the VT/VF detection algorithm of the apparatus of FIG. 2;

FIG. 4A illustrates the operation of the VT/VF detection algorithm of FIG. 4 when a missed interval occurs;

FIG. 5 illustrates reconfirmation in the initial shock sequence;

FIG. 5A illustrates spontaneous reversion before a first reconfirmation;

FIG. 5B illustrates spontaneous reversion before a second reconfirmation;

FIG. 5C illustrates spontaneous reversion and redetection.

FIG. 6 illustrates reconfirmation in the subsequent shock sequence;

FIG. 6A illustrates the charge sequence after a failed shock;

FIG. 6B illustrates spontaneous reversion following a shock;

FIG. 6C illustrates spontaneous reversion followed by degeneration of sinus rhythm to VT/VF;

FIG. 7 illustrates reconfirmation after the last shock; and

FIG. 7A illustrates a successful last shock in a series.

DEFINITION OF TERMS

Absolute Refractory Period (ARP)

Figure 1:
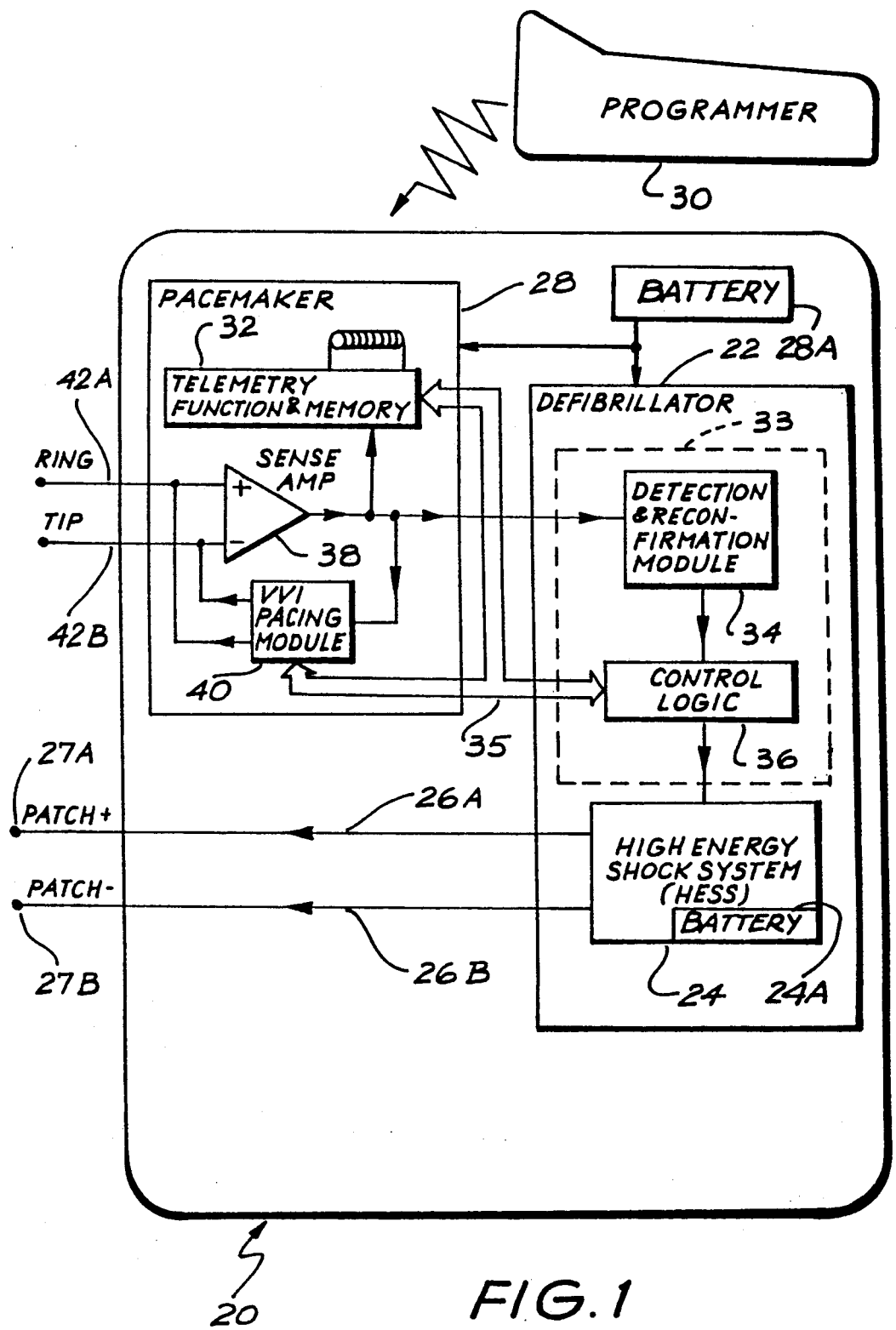
FIG. 1 is a system block diagram of a combined multi-programmable telemetric implantable defibrillator and bradycardia pacing apparatus in accordance with the invention.

The period of time which occurs after a sensed event during which further events, of any nature, are not sensed or counted.

Auto Shock Sequence

A charge sequence that is initiated by detection of tachycardia. Reconfirmation occurs during the sequence and may result in delivery of a shock.

Automatic Detection

With tachycardia detection programmed on and defibrillation function programmed on, 6 out of 7 intervals which fall within the Tachycardia Detection Interval (TDI) will be required for recognition of tachycardia.

BOL

Beginning of life.

Bradycardia Support

The VVI pacing portion of the apparatus.

Charge Sequence

The chain of events from initiation of energy incrementation until either a shock to the patient is delivered or an internal (dump) discharge occurs.

Defib Standby Condition

The condition that exists when:
A. Defib is on.
B. Tachycardia detection is on, and
C. Energy is at the programmed initial value.

Defib Test

The defibrillation capacitors are charged to 650 V and then dump discharged. The charge time is measured and is available for recording purposes. This test is performed via telemetry.

Dump Discharge

The delivery of energy to a load within the case.

EOL

End of Life

EMI

Electro-magnetic interference.

EMI Detection Window (EDW)

A window which is placed after the absolute refractory period (from 44 to 76 ms after a sensed event).

EMI Detection Algorithm

EMI is recognized when 15 sensed intervals fall within the EMI Detection Window.

Full Charge

State of the defibrillator capacitors when charged to required voltage.

HESS

High Energy Shock System consisting of a DC to DC converter, a low impedance battery, capacitor for energy storage, and a number of high voltage/high current switches to discharge the stored energy externally or internally.

Incrementing Energy

An incrementing sequence of energies defined by the initial programmed energy.

Initial Energy

The first energy level to which the defibrillator charges in an initial auto shock sequence.

Initial Shock Sequence

The first shock sequence in an auto shock series.

Interference Reversion Mode Pacing—(IRM) Pacing

When EMI has been detected for a full standby interval, VOO pacing will continue at the programmed standby rate until EMI is no longer detected.

Manual Charge Command

A command issued via the programmer to the apparatus, during execution of which no detection or reconfirmation occurs). A discharge is delivered when the full charge is met. This can be done with either of 2 commands: max shock or manual shock.

Maximum Shock

A command issued by the programmer for a 30 J manual defibrillation shock.

Maximum Time to Shock

The maximum time to the delivery of a shock after detection, set at 30 seconds.

Minimum Time to Shock

This is the earliest a discharge will be delivered after detection.

Maximum Number of Shocks in a Series

The programmable maximum number of shocks that will be delivered during one series starting with the initial sequence. The maximum number programmable is 7.

NSR

Normal Sinus Rhythm.

Onset

The start of any shock sequence.

Reconfirmation

When the apparatus is in an automatic shock sequence there are two points of reconfirmation: at the programmed minimum time to shock and after the full charge has been reached or at 30 seconds, whichever comes first. Reconfirmation involves testing the tachycardia detection output (TDO)—if the TDO is high, reconfirmation occurs—if the TDO is low, reconfirmation will not occur and the apparatus will subsequently dump the discharge. Two reconfirmations must occur before a shock is delivered to the patient. If the TDO is low at either reconfirmation, the shock will be dumped.

Sensed Event

Cardiac electrical event detected by the circuitry of the apparatus.

Subsequent Shock Sequence

Any shock sequence after the first (in the same series) which occurs due to reconfirmation of the tachycardia.

SVT

Supra-ventricular tachycardia.

Tachycardia Detection Interval (TDI)

The tachycardia detection interval defines the size (maximum width) of the tachycardia detection window (TDW). When 6 out of 7 sensed events occur inside this TDW, detection occurs.

TDO

Tachycardia Detection Output.

Tachycardia Detection Window (TDW)

The interval from 76 ms after any sensed event until the elapsed TDI.

VF

Ventricular fibrillation or flutter.

VT

Ventricular tachycardia.

VT/VF Detection Algorithm

The TDO is high if at least 6 out of the last 7 sensed intervals fall within the TDW. The TDO is low if at least 2 sensed events of the last 7 sensed intervals are longer than the TDW or if EMI has been detected.

DETAILED DESCRIPTION OF THE DRAWINGS

FIG. 1 illustrates an overview of an encased combined multi-programmable telemetric implantable defibrillator and bradycardia pacing apparatus 20. Apparatus 20 contains a defibrillator 22 including a HESS (High Energy Shock System) 24 connected by defibrillation leads 26A and 26B to defibrillation patches 27A and 27B, respectively, to revert ventricular tachycardia (VT) or ventricular fibrillation (VF) to normal sinus rhythm (NSR). Defibrillation patches 27A and 27B may be epicardial or of endocardial. Additionally the apparatus contains a multi-programmable VVI bradycardia support system or pacemaker 28.

A hand-held telemetric programmer 30 for apparatus 20 is suitable for use with an interface module, a printer, and an external telemetry coil (all not shown).

A telemetry unit 32 within pacemaker 28 of apparatus 20 interfaces with the internal components of pacemaker 28 and defibrillator 22. Defibrillator 22 includes a control unit 33 having a detection and reconfirmation module 34, and a control logic module 36 as well as the high energy shock system 24 (HESS). Control unit 33 controls VT/VF detection and defibrillation therapy. Each of these functions can be programmed independently of the other functions and may be programmed to ON or OFF. High energy shock system 24 includes a DC to DC converter which provides an isolated high voltage output, a low impedance battery, a capacitor (or capacitors) for energy storage, and high voltage/high current switches to discharge the stored energy externally to the patient by means of defibrillation leads 26A and 26B and defibrillation patches 27A and 27B, or internally to the apparatus by means of a dump discharge.

Pacemaker unit 28 contains a sense amplifier 38 and a VVI pacing module 40 connected to the ring lead 42A and tip lead 42B of a bipolar sensing and pacing lead system (not shown) which may be epicardial or endocardial. A defibrillation and EMI protection circuit (not shown) protects the circuitry of pacemaker 28 from signals of high amplitude which may be picked up by leads 42A and 42B.

Control logic module 36 of unit 33 of defibrillator 22 interfaces with pacing module 40 of pacemaker 28 and telemetry unit 32 thereof to provide bidirectional communication with the programmer 30 and for interaction with the pacing and sensing functions. Digital communication signals are carried by a bidirectional data bus 35. Analog signals from sense amplifier 38 are provided to telemetry unit 32 and to detection and reconfirmation module 34. Control unit 33 may comprise a digital CMOS integrated circuit which also interfaces to HESS 24.

There may be two separate energy sources for apparatus 20. Pacemaker 28, including telemetry unit 32, and the defibrillator control unit 33 may be powered by means of a standard lithium iodine pacer cell 28A. HESS 24 including its DC/DC converter may be powered by means of a lithium silver vanadium pentoxide cell 24A.

Bradycardia Support

Pacemaker 28 of apparatus 20 functions as a programmable bradycardia support pacemaker which preferably provides VVI pacing. However dual chamber pacing may also be provided. For VVI pacing, the sensitivity selected is used to sense both sinus rhythm and ventricular arrhythmias. There are seven programmable values ranging from 0.7 mV to 4.5 mV.

The pulse amplitude selected is used for bradycardia support pacing. There are two programmable values, 2.5 V and 5.0 V. The pulse amplitude decreases with pacemaker cell depletion but the characteristics of the power source enable the BOL values to be maintained throughout the major part of the life of the device.

The pulse width selection is used for bradycardia support pacing. There are four programmable values ranging from 0.25 ms or 1.0 ms.

The standby rate is shown below. There are sixteen steps in 5 BPM increments from 30 to 105 BPM. Not all rates are obtainable with all tachycardia detection intervals (TDI).

| TDI (ms) | Highest allowable standby rate (BPM) |
|---|---|
| 412 | 75 |
| 384 | 80 |
| 352 | 85 |
| 320 | 90 |
| 288 | 95 |
| 256 | 100 |

Hysteresis applies only to bradycardia pacing. This function extends the standby interval by the programmed value after a sensed event. The programmable values include 0 (no extension), 125, 250 and 375 ms.

Pacemaker 28 operates in VVI mode except under the following conditions:

1. When EMI has been detected (VOO pacing is provided at the standby rate).

2. When taking lead impedance measurements and cell impedance measurements (VOO pacing is provided at the rate of 85-100 BMP).

3. When performing a threshold test (VOO pacing is provided at a rate of 85-120 BMP).

4. During loss of sensing (VOO pacing is provided at the standby rate).

5. During programming (Magnet interval ±125 ms, 85-100 BMP). It is to be noted, however, that VOO is not a programmable mode.

Pacemaker 28 may have an internal magnetically activated switch (not shown) so that when a magnet is applied to the skin of the patient over apparatus 20, all functions (including both bradycardia support and defibrillation) are disabled as long as the magnet remains in position. As an alternative, the system may be configured so that bradycardia support remains on.

Defibrillation Therapy—Shock Delivery

Apparatus 20 preferably delivers synchronized defibrillation shocks, i.e. the shocks are synchronized with the R-wave of the patient's cardiac rhythm.

The initial energy refers to defibrillation energy that is used in the initial charge sequence. There are twelve programmable initial energies available. These initial energies are 3, 4, 7, 9, 10, 13, 16, 18, 21, 25, 28 and 30 J which are nominal values into a 50 ohm load.

Energy incrementation occurs only in an auto shock sequence. After a shock is delivered at the initial energy and tachycardia has been reconfirmed, the energy is automatically incremented (if not already at 30 J).

The fourth and subsequent shocks in a series are delivered at the maximum energy of 30 J irrespective of the programmed initial energy. Alternatively, the system may be configured so that the user can program the energy level for later shocks.

The number of shocks delivered in a series is programmable from 4 to 7. If the last programmed shock in a series has been delivered, and tachycardia is reconfirmed 6 seconds after the last shock, the defib function will turn off automatically. Bradycardia support function is not, however, affected. Reactivation of the defibrillator function and the tachycardia detection is accomplished by using the programmer.

If tachycardia is not reconfirmed 6 seconds after delivering the last shock in a series, then the defibrillation function remains ON, no dump discharge occurs, and the capacitors will not be charged. The total shock counter is incremented, however, and the device returns to DEFIB STANDBY condition.

The defibrillation waveform is a truncated exponential with programmable leading edge voltage amplitude and pulse width. The selected amplitudes and pulse widths deliver energies from 3 to 30 J into a 50 ohm load. The amplitude is programmable between 250 V and 650 V and the pulse width between 6 and 12 ms to deliver energy in the range of 3 to 30 J. The exact energy delivered depends on the impedance across the defibrillation patches.

HESS 24 may be disabled by means of magnet application or using the programmer to either turn the implant off or to turn off the defibrillation function.

Apparatus 20 is configured to respond to a manual charge command. This manual shock facility is used for testing. During this sequence, no detection, reconfirmation, or incrementing of energy may occur. Each shock must be initiated by the programmer. If it is desired to prevent a manual shock from being delivered to a patient, a magnet must be held in place for 30 seconds or more.

For emergency situations, there is a max shock command. As is the case for the manual shock command there can be no detection, reconfirmation, or energy incrementation while in this sequence. This function has priority over all other functions and is initiated by a command from the programmer. To prevent a maximum (max) shock from being delivered, a magnet must be held in place for at least 30 seconds.

Independently of the previously programmable values of initial energy, tachycardia detection, and whether the device is turned on or off, a maximum shock of 30 J is delivered.

The charging of the defibrillator capacitors starts immediately upon confirmation of tachycardia and continues until full programmed energy is reached or for 30 seconds (whichever occurs first). If a full charge has not been reached in 30 seconds, the accumulated energy in the capacitors will be delivered to the patient at the programmed pulse width. Thus, from the time of detection, the maximum time to shock is 30 seconds unless the charged is internally dumped.

The minimum time to initial shock can be programmed to either 6 seconds or less, or 20 seconds. This time will be 6 seconds unless programmed to another value.

The minimum time to subsequent shock is always 6 seconds from the time of the previous shock.

Defibrillation Therapy—Initial Shock Sequence

The tachycardia detection output (TDO) controls the auto shock series. The initial shock sequence differs from subsequent shocks in that series.

The usual functional mode of the device is called the defib standby condition which is:
defibrillator—on
tachycardia detection—on
energy—at programmed initial value.

A charge sequence can only take place during an auto shock series, or by the introduction of a manual shock or max shock charge command.

Reconfirmation, as shown in the preferred embodiment, occurs twice as an added safety factor. That is, there are two reconfirmations after detection of a VT/VF and prior to delivering a shock. Reconfirmation occurs (1) at the minimum time to shock, and (2) at full charge of the capacitor or 30 seconds, whichever occurs first.

Figure 2:
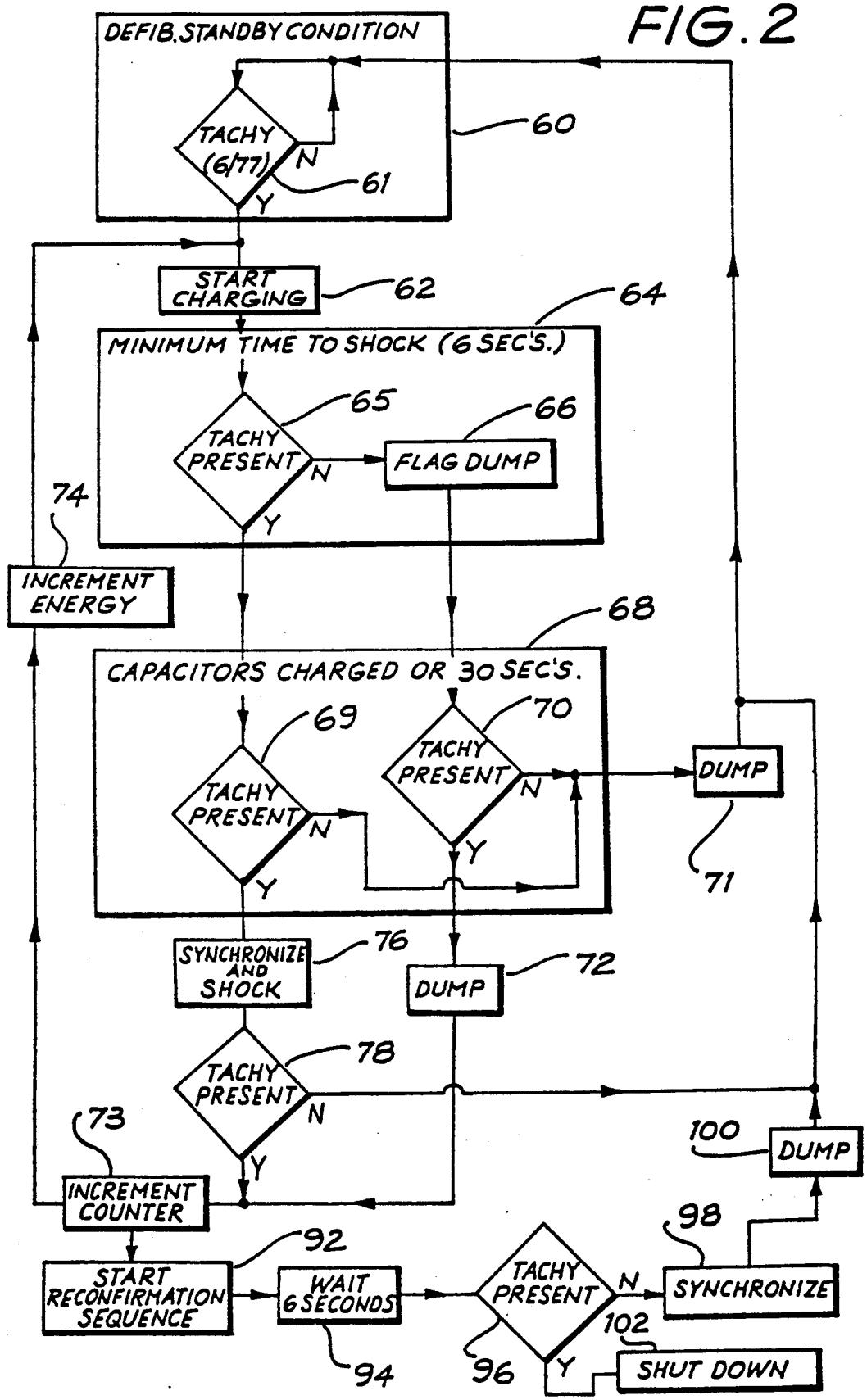
FIG. 2 is a logic flow diagram of the operation of the defibrillator of the apparatus of FIG. 1.

Referring to FIG. 2, the order of events for the initial shock sequence starts at block 60 where defibrillator 22 is in the base state or standby condition. When the TDO is high because at least 6 out of the last 7 sensed intervals fall within the TDW, at step 61, branching to step 62 occurs. HESS 24 starts to charge to the initial energy. After a delay equal to the programmed minimum time to shock, reconfirmation of TDO will occur at block 64. Specifically, if the TDO is low, branching occurs from step 65 to step 66 where a dump discharge is flagged. In either event, at 68 the remainder of capacitor charging by HESS 24 is completed.

A second reconfirmation in block 68 occurs at full charge or 30 seconds, whichever comes first. If the TDO was low at step 65 and a flag was set for dump at step 66, then at step 70, if the TDO is low, a dump occurs at 71 and the defibrillator returns to the standby condition of block 60. However, if at 70 the TDO is high, the dump occurs at 72, a shock counter is incremented at 73 and the energy is incremented at step 74.

If the TDO is low at step 69, then a dump occurs at step 71 and the defibrillator returns to block 60. If there is reconfirmation (i.e. TDO is high) at both steps 65 and again at step 69, then a synchronized defibrillation shock is delivered to the patient at 76.

If charging takes place rapidly, which is generally the case unless the highest shock energies (and therefore the highest voltages) are used, the capacitors may be fully charged to the appropriate voltage and block 68 may introduce only a delay of approximately 2.0 ms needed to check the TDO while step 76 introduces only the delay needed to synchronize the beginning of the shock to the R-wave of the patient's heart.

At step 78, the TDO is again checked at a time 4.0 ms after a shock has been delivered. If the TDO is still high, branching to step 73 occurs. The energy counter is incremented to the next energy level at step 74, and a subsequent shock sequence is started at step 62. If the TDO is low (there is no tachycardia), reversion has occured and defibrillator 22 returns to the standby condition at 60.

It will be understood that during any traversal of the flow chart of FIG. 2, if the TDO is high at 65 and low at 69, the charge will be internally dumped and defibrillator 22 returns to block 60. If the TDO is low at 65 and high at 70, an internal dump will take place and the energy level, if less than 30 J, will be incremented.

Counter 73 (in control logic 36) counts the total number of shocks delivered. After the programmed number of shocks has been delivered, the counter is reset to its initial value and branching from step 73 to step 92 occurs where a new reconfirmation sequence is initiated, but the defibrillation capacitors are not charged. A delay of six seconds is initiated at step 94. At step 96, a determination is made as to whether tachycardia still is present. If not, the circuitry executes a synchronize operation at step 98 and a "dump" operation at step 100, even though charging has not occured, and defibrillator 22 returns to the standby condition at 60. If a tachycardia is still present at 96 (TDO high), then defibrillator 22 shuts down at step 102 until reactivated by programmer 30, although bradycardia support pacing from pacemaker 28 is still available.

If at any one of steps 65, 69 or 70 there is no reconfirmation (i.e., TDO is low) then a dump discharge occurs and no defibrillation shock is delivered to the patient.

Figure 2A:
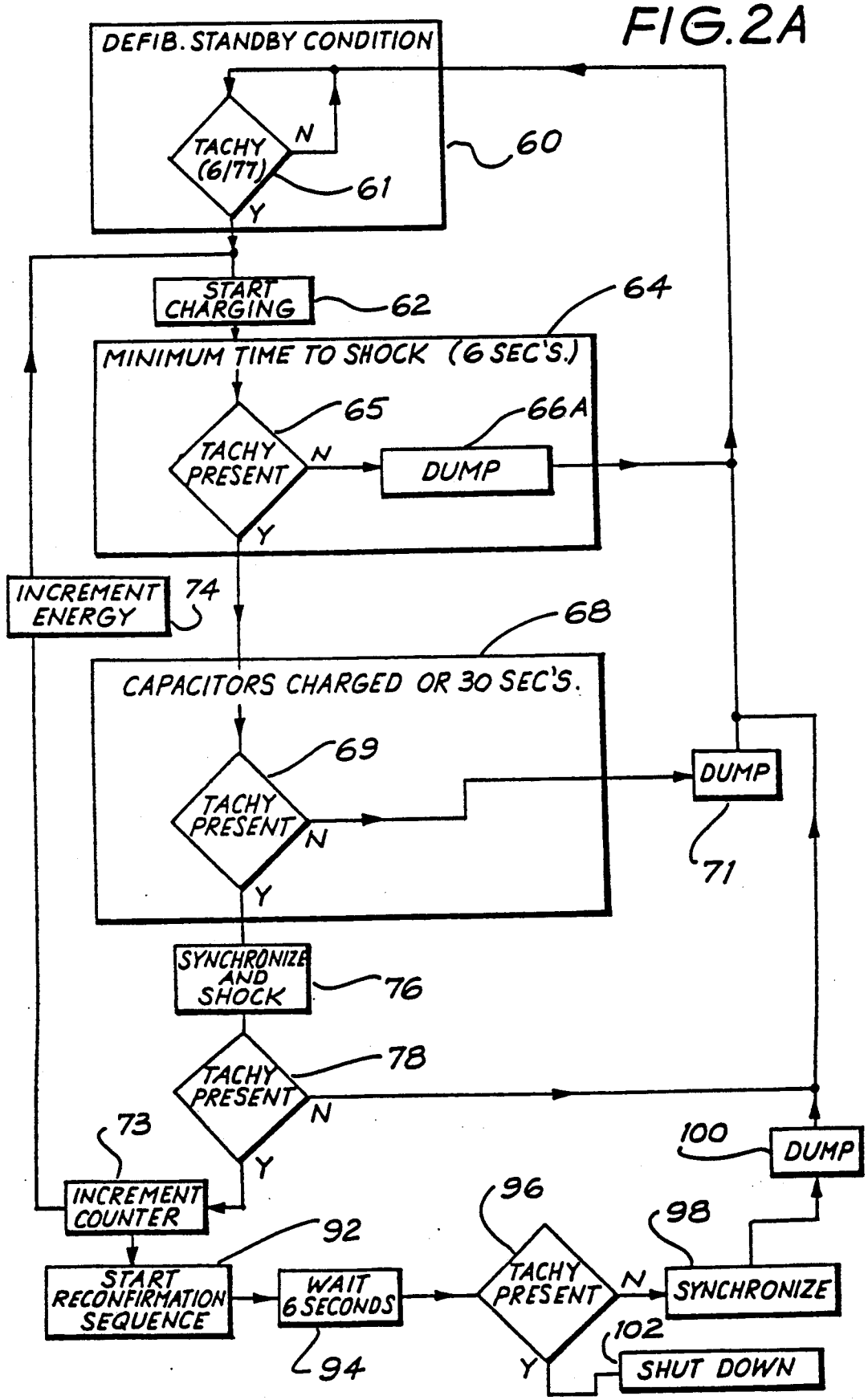
FIG. 2A is an alternative logic flow diagram of the operation of the defibrillator of the apparatus of FIG. 1.

FIG. 2A illustrates another embodiment of a flowchart for the operation of defibrillator 22. The operation of the flowchart of FIG. 2A is similar to that of FIG. 2 except for the following. If the TDO is not high at step 65 then branching occurs to step 66A, a dump discharge occurs and the defibrillator returns to the standby condition at block 60.

If the TDO is low at step 69, branching to step 71 follows, a dump occurs and the defibrillator returns to the standby condition at block 60. In other words, the charge is dumped unless the TDO is high at both step 65 and step 69. If the TDO is high at both steps, a sychronized shock is delivered at step 76. The TDO is again checked at step 78.

As noted above with respect to FIG. 2, at all but the highest energy levels, the capacitors in defibrillator 22 are generally fully charged in the time interval controlled by block 64. As a result, the additional delay prior to delivery of a shock at step 76 above that introduced by block 64 is that delay introduced by block 68 that is necessary to determine the state of the TDO (2.0 ms at step 69) and the time needed to synchronize the shock to the R-wave of the patient's heart at step 76.

Operation in accordance with the flowchart of FIG. 2A has the advantage of returning to the standby condition sooner in the event that tachycardia again occurs. In addition, when the programming calls for higher energies, if the TDO is low at step 65 there is an immediate dump at step 66A and a return to the standby condition thus saving the energy required for further charging of the capacitors at block 68.

VT/VF Detection and EMI Detection

Figure 3:
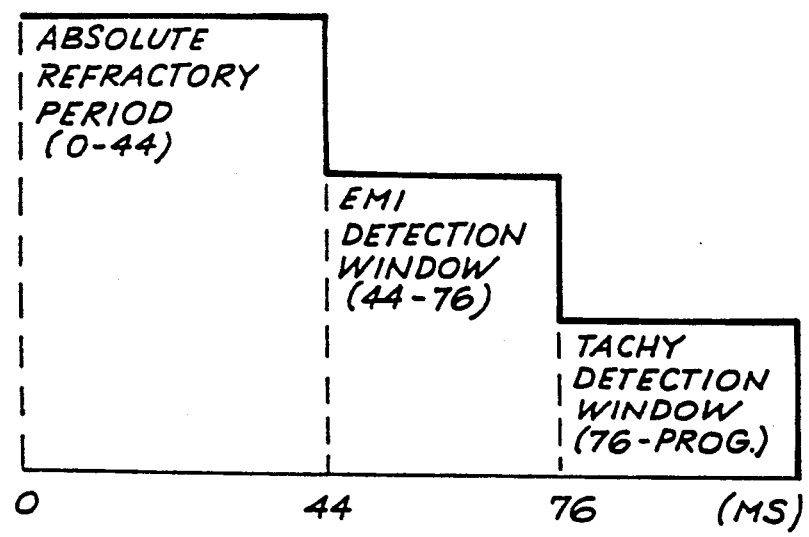
FIG. 3 illustrates the relationship between the absolute refractory period (ARP), the electromagnetic interference (EMI) detection window (EDW), and the tachycardia detection window (TDW) of the apparatus of FIG. 1.

The VT/VF detection and reconfirmation module 34 and an EMI detection module (not shown) within pacing module 40 are simultaneously active. Referring to FIG. 3, there is depicted the relationship between the absolute refractory period (ARP), the EMI detection window (EDW), and the tachycardia detection window (TDW). As sensed signals are detected, the time between signals is measured, and the resulting intervals are classified according to the detection window into which they fall. As each interval is classified, it is counted, and when a predetermined number of intervals have accumulated, the EMI or VT/VF state is reached. These predefined conditions are described in further detail below.

The VT/VF detection in apparatus 20 relies on pacemaker sense amplifier 38 and an algorithm based on the last seven sensed intervals implemented in module 34.

Tachycardia detection (tachy detect) may be programmed on or off. When tachy detect is off no tachycardia detection, confirmation or reconfirmation can occur. In this state the device may be manually operated using the programmer to deliver manual defibrillation shocks, including max shock. Therefore, tachycardia detection must be programmed on for automatic detection and reconfirmation to operate.

The absolute refractory period (ARP) is set on a sensed event and extends until 44 ms after that event is sensed. The EDW occurs from 44-76 ms after the event is sensed. The TDW occurs from 76 ms to the elapsed TDI. In FIG. 3 the elapsed TDI value is 224 ms. After any sensed event the EDW is opened from 44 ms after and stays open until 76 ms after the sensed event has been detected. The TDW is blanked while the EDW is open. The TDW is opened from 76 ms after a sensed event, until the next sensed event, or until the TDI has elapsed (224 ms).

The presence of EMI is confirmed if the last 15 sensed intervals fall within the EMI detection window (EDW). When EMI is detected for several standby pacing intervals, the device reverts to VOO pacing at the programmed standby rate. The EMI detection condition is reset when two consecutive intervals are detected outside the EDW.

FIG. 4 illustrates the operation of the VT/VF detection algorithm. The VT/VF detector counts those sensed intervals that are within the TDW. When 6 out of the last 7 of these intervals satisfy this condition, the TDO is set high. The TDO is low if at least 2 sensed intervals of the last 7 sensed intervals are longer than the TDW, or if EMI has been detected. If the TDO is high, bradycardia pacing is disabled. If some of these intervals fall within the EDW, they are ignored by the VT/VF detection circuitry. The TDW in FIG. 4 extends from 76 ms from a sensed event until the programmed value of the tachycardia detection interval (TDI), or the next sensed event, whichever comes first. As shown at 1-2, a sensed event occurs in conjunction with each R wave. As shown at 3-4, during NSR the TDW is opened 76 ms after the sensed event. The TDW then closes at TDI as no other events are detected before the programmed TDI elapses. As shown at 5-9, VT/VF occurs and sensed events occur more quickly. The sensed events arrive before a TDI has elapsed, and six intervals are counted by the VT/VF detector. As shown at 10, six of the previous seven intervals have fallen within the TDW, and the TDO is therefore set to high, at 11.

FIG. 4A illustrates the use of the VT/VF detection algorithm with a missed interval. As shown at 1-2, sensed events occur in conjunction with each R-wave. As shown at 3-4, another sensed event does not arrive before the programmed TDI, so the TDW is closed at TDI. At 5-9 with the occurrence of VT/VF, sensed events arrive more frequently (before the programmed TDI has elapsed). The VT/VF detector has now counted five of the last seven sensed intervals longer than 76 ms and less than the programmed TDI. At 10, a reaction in the VT/VF signals results in no further sensed events before a TDI has elapsed. At the end of the TDI, the TDW is closed. The sensed signals are not seen as tachycardia by the VT/VF detector. At 11, the interval between the next two sensed events is inside the TDW. This interval is counted by the VT/VF detector, thereby accumulating six tachycardia intervals of the last seven intervals sensed. As shown at 12, six of the previous seven intervals have fallen within the TDW, so the TDO is set high.

The invention will be more readily understood with reference to FIG. 5, FIG. 5A, FIG. 5B, and FIG. 5C, which provide examples of the apparatus using reconfirmation in initial shock sequences.

FIG. 5 illustrates an initial shock sequence. Initially the TDO is low due to appropriate sensing of sinus rhythm. As shown at 1-6, short intervals are sensed after the onset of VT/VF. At 7, it is shown that six out of seven intervals fall within the TDW. The TDO is then set high, and HESS 24 starts charging the capacitors. At 8, the first reconfirmation (RC) point (at, for example, six or twelve seconds), the TDO is still high and VT/VF is confirmed. At 9, the second reconfirmation point, (at full charge or at thirty seconds, whichever comes first), TDO is still high and VT/VF is therefore reconfirmed. At 10, a defibrillation shock is delivered to the patient. At 11, the TDO is reset to low as two intervals sensed are longer than the TDI. The apparatus then returns to the defib standby condition.

FIG. 5A illustrates an example of an initial shock sequence with spontaneous reversion before the first reconfirmation. Initially the TDO is low due to sensing of sinus rhythm. As shown at 1-6, short intervals are sensed following the onset of tachycardia. At 7, six out of seven intervals are inside the TDW. The TDO is then set high and the HESS 24 starts charging. At 8-9, two intervals longer than the TDI are sensed due to the spontaneous reversion to NSR. At 10, the TDO resets to low as there are no longer six out of seven intervals inside the TDW. At 11, the first reconfirmation occurs at six seconds after detection. As the TDO is low, VT/VF is not confirmed, so although the discharge is "flagged" to dump, charging continues to the programmed voltage. At 12, the second reconfirmation point (at full charge or thirty seconds, whichever comes first), TDO is low and VT/VF is not reconfirmed. The apparatus dumps the energy internally. The device then returns to the defib standby condition.

FIG. 5B illustrates an example of spontaneous reversion before the second reconfirmation in an initial shock sequence. The TDO is low initially due to appropriate sensing of sinus rhythm. At 1-6, there is shown the sensing of short intervals at the onset of VT/VF. At 7, six out of seven intervals are inside the TDW. The TDO is set to high and the HESS starts charging the capacitors. At 8, the first reconfirmation point (at six or twelve seconds), the TDO is still high and VT/VF is confirmed. Spontaneous reversion of the VT/VF to NSR occurs soon afterwards. At 9, two intervals longer than the TDI are sensed and thus the TDO resets to low. HESS 24 continues to charge the capacitors. At 10, the second reconfirmation point (at full charge or thirty seconds, whichever comes first), the TDO is low and VT/VF is not reconfirmed. The discharge is dumped internally and no energy is delivered to the patient. The apparatus then returns to the defib standby condition.

FIG. 5C illustrates an example of an initial shock sequence of spontaneous reversion and redetection. The TDO is initially set to low due to appropriate sensing of sinus rhythm. As shown at 1-6, short intervals are timed inside the TDW. At 7, the TDO is set high and the apparatus begins charging the capacitors. At 8-9, there is a spontaneous reversion of the VT/VF to NSR, and two intervals are timed outside the TDW. At 10, the TDO is reset to low. At 11, the first reconfirmation point, the TDO is low, so the discharge is "flagged" to be dumped. At 12-17, sinus rhythm degenerates into VT/VF and short intervals are timed inside the TDW. At 18, the TDO is set high as six intervals have been detected inside the TDW. At 19, the second reconfirmation point, the TDO is high but as the discharge was "flagged" to be dumped, a dump discharge occurs, although the energy is incremented and charging commences for the next shock.

Defibrillation Therapy—Subsequent Shocks in a Series

For subsequent shocks, the following sequence is repeated until the programmed maximum number of shocks in the series have been delivered, or until tachycardia is no longer detected.
 (i) If the TDO is high, charging to the next energy level in the incrementing energy table begins.
 (ii) There is a first reconfirmation of the TDO at the minimum time to shook (at six seconds) at step 65 (FIG. 2).
 (iii) There is a second reconfirmation of the TDO at full charge or thirty seconds, whichever comes first at step 69 (FIG. 2).
 (iv) If reconfirmation occurs (TDO goes high), at (ii) and (iii), a shock is delivered to the patient. If at either (ii) or (iii) VT/VF is not reconfirmed (TDO is low) then a dump discharge will occur.
 (v) If, at step 78, the TDO is low, the apparatus will return to the defib standby condition. If at step 78, the TDO is high, then the above sequence is repeated.

The invention will be more readily understood with reference to FIG. 6, FIG. 6A, FIG. 6B and FIG. 6C which provide examples of the operation of the device using reconfirmation in a subsequent shock sequence.

Referring now to FIG. 6, there is depicted an example of a subsequent shock sequence. At 1, there is shown the first reconfirmation point in the second charge sequence. The TDO is high as VT/VF is confirmed. At 2, the second reconfirmation point (at full charge or thirty seconds, whichever comes first), VT/VF is still detected and the TDO remains high. At 3, a shock is delivered to the patient reverting the VT/VF to sinus rhythm. At 4, two intervals are sensed outside the TDW causing the TDO to reset to low.

Referring now to FIG. 6A, there is depicted an example of a charge sequence after a failed shock. As shown at 1, a previously programmed shock is delivered to the patient. The shock fails to revert the tachycardia and as the TDO is high, charging begins once more to the next incremented energy level. At 2, the six second reconfirmation point, the TDO is high and VT/VF is confirmed. Charging continues. At 3, the capacitors are charged to the programmed voltage and the apparatus reconfirms VT/VF. The TDO is still high. At 4, a shock is delivered to the patient. As shown at 5, after two intervals are detected outside the TDW, the TDO resets to low.

FIG. 6B illustrates an example of spontaneous reversion following a shock. As shown at 1, the TDO is high and a shock is delivered to the patient, but fails to revert the tachycardia. The energy increments and charging recommences. At 2, the VT/VF reverts spontaneously. At 3-4, the reversion is followed by a pause which equals the programmed bradycardia support standby interval. Bradycardia support pacing is initiated and two paced beats occur. At 5, there is shown the first reconfirmation point (at six seconds since charging started). The TDO is still high and the device reconfirms VT/VF (even though the patient is in sinus rhythm). At 6, two intervals of the last seven have been timed outside the TDW, so the TDO resets to low. At 7, higher rate sinus rhythm returns and further pacing is inhibited. At 8, the capacitors are charged to the programmed voltage and the second reconfirmation point is reached. VT/VF is not confirmed, so the energy is dumped. The apparatus then returns to the defib standby condition.

FIG. 6C illustrates an example of spontaneous reversion followed by degeneration of sinus rhythm to VT/VF in a subsequent shock sequence. At 1, a shock is delivered which subsequently reverts the VT/VF. Charging recommences as the TDO remains high. At 2, two intervals outside the TDW are sensed and TDO is reset to low. At 3, at the reconfirmation point (six seconds after 1), the TDO is low and the discharge is "flagged" to be dumped. At 4-10, VT/VF resumes and six intervals are timed in the TDW. The TDO is reset to high. At 11-12, at the second reconfirmation point, the TDO is high indicating VT/VF. However, as this discharge was "flagged" to be dumped, a dump occurs at 12 and charging recommences, this time to a higher energy. As shown at 13 and 14, at the next two reconfirmation points, VT/VF is confirmed, and a shock is delivered to the patient at 15.

Defibrillation Therapy—Reconfirmation After Last Shock

As described above, reconfirmation of the TDO occurs at 6 seconds after the last allowable shock in a series. If the TDO is high, then the defibrillator function will automatically turn off. If the TDO is low, then the defibrillator function will return to the defib standby condition.

The invention will be more readily understood with reference to FIG. 7 and FIG. 7A which provide examples of the operation of the device depicting reconfirmation after the last shock.

FIG. 7 illustrates an example of reconfirmation after the last shock in a series. At 1, the last shock in a series is delivered. Charging does not commence even though the TDO is high. At 2, at the reconfirmation point (at six seconds after the previous shock), VT/VF is reconfirmed. The defibrillator function turns off. Bradycardia support pacing is still available if the TDO is reset to low and no cardiac electrical events are detected.

FIG. 7A illustrates an example wherein in the last shock is successful. At 1, the last shock in a series is delivered and causes asystole. Charging does not recommence even though the TDO is high. At 2-3, as no sensed events occur during a standby interval (at 2), bradycardia support pacing commences. At 4, at the reconfirmation point six seconds after delivery of the last shock, the TDO is low. The apparatus returns to the defib standby condition and if another episode of VT/VF is detected, defibrillation shocks will be delivered.

The use of a sensing lead separate and apart from the defibrillation patches is believed to be of great importance to the operation of the invention. The signals produced by the defibrillation patches are generally of such large amplitude that sense amplifiers are saturated. The isolation provided by a separate sensing lead avoids this problem.

While the invention has been discussed with reference to a defibrillator which supplies relatively high energy shocks which are synchronized to the R-wave of the patient's heart, it will be understood that the principles of the invention may be applied to any form of cardioversion whether synchronized to the R-wave or not, and to countershocks of any level.

Although the invention has been described with reference to specific embodiments, it is to be understood that these embodiments are merely illustrative of the application of the principles of the invention. Numerous modifications may be made thereon and other arrangements may be devised without departing from the spirit and scope of the invention.

What is claimed is:

1. An apparatus for treating a tachyarrhythmia of the heart comprising:
    detection means for detecting a tachyarrhythmia;
    shock means for delivering a shock to the heart; and
    reconfirmation means for confirming a presence of the tachyarrhythmia subsequent to detection by said detection means and for reconfirming the presence of the tachyarrhythmia immediately prior to delivery of a shock by said shock means, said reconfirmation means controlling said shock means so that only if the presence of said tachyarrhythmia is both confirmed and reconfirmed does said shock means deliver said shock to the heart, said reconfirmation means confirming the presence of said tachyarrhythmia at a first predetermined time after detection of said tachyarrhythmia by said detection means, and reconfirming the presence of said tachyarrhythmia at a second time after detection by said detection means, said second time being no greater than a second predetermined time after said first time.

2. The apparatus of claim 1, wherein said shock means includes at least one capacitor, a discharge means for discharging to the heart energy stored in said at least one capacitor, and means for supplying over time, a predetermined quantity of energy to said at least one capacitor, and wherein said second predetermined time coincides with termination of the earlier of a fixed interval after detection by said detection means or an interval required to supply said predetermined quantity of energy to said at least one capacitor.

3. An apparatus for treating a tachyarrhythmia of the heart comprising:
    detection means for detecting a tachyarrhythmia;
    shock means for delivering a shock to the heart; and
    reconfirmation means for confirming a presence of the tachyarrhythmia subsequent to detection by said detection means and for reconfirming the presence of the tachyarrhythmia immediately prior to delivery of a shock by said shock means, said reconfirmation means controlling said shock means so that only if the presence of said tachyarrhythmia is both confirmed and reconfirmed does said shock means deliver said shock to the heart,
    said detection means comprising:
    means for defining a tachycardia detection window for sensed events;
    means for determining whether at least a predetermined portion of said sensed events fall within said window; and
    means for providing an output signal to said reconfirmation means when at least said predetermined portion of sensed events fall within said window.

4. The apparatus of claim 3, wherein said predetermined portion is equal to six out of a last seven of said sensed events.

5. A method for treating tachyarrhythmias of the heart comprising the steps of:
    a) detecting a tachyarrhythmia;
    b) reconfirming whether said tachyarrhythmia exists at at least one time after detecting said tachyarrhythmia; and
    c) delivering a shock to the heart only if at said step of reconfirming whether said tachyarrhythmia exists, a presence of said tachyarrhythmia is reconfirmed, one of said at least one times being immediately prior to delivering said shock,
    said method further comprising the steps of:
    commencing charging of a capacitor when said tachyarrhythmia is detected;
    reconfirming the presence of said tachyarrhythmia at a first predetermined time; and
    discharging the charge on said capacitor to a load other than the heart if said presence of said tachyarrhythmia is not confirmed at said first time,
    said method still further comprising the steps of:
    again reconfirming the presence of said tachyarrhythmia at a second time, said second time being a shorter of a second predetermined time or the time required for said capacitor to charge to a predetermined energy level, and
    supplying a shock to the patient by discharging said capacitor into the heart if said tachyarrhythmia is present at said first time and at said second time.

6. The method of claim 5, further comprising the step of discharging the capacitor to a load other than the heart if said tachyarrhythmia is not present at said second time.

7. The method of claim 5, further comprising the steps of:
    again charging said capacitor after said defibrillation shock is delivered to the heart, said charging being to a higher energy level than that of said first shock, and repeating steps a) to c).

8. The method of claim 7, further comprising repeating recharging said capacitor to a higher energy level and steps a) to c) until the earlier of when said tachyarrhythmia has reverted or a predetermined number of shocks have been delivered.

9. The method of claim 8, wherein said predetermined number of shocks is selected to be between four and seven shocks.

10. The method of claim 7, further comprising, subsequent to delivering said shocks and prior to again charging said capacitor, the step of:

again determining whether said tachyarrhythmia exists, and if said tachyarrhythmia is not present, again detecting subsequent tachyarrhythmias.

11. A method for treating tachyarrhythmias of the heart comprising the steps of:

a) detecting a tachyarrhythmia;

b) reconfirming whether said tachyarrhythmia exists at at least one time after detecting said tachyarrhythmia; and c) delivering a shock to the heart only if at said step of reconfirming whether said tachyarrhythmia exists, a presence of said tachyarrhythmia is confirmed, one of said at least one times being immediately prior to delivering said shock, said step of confirming whether a tachyarrhythmia exists comprising:

sensing a series of events of the heart;

defining a tachycardia window during which a number of sensed events of the heart occurs; and recognizing the presence of a tachyarrhythmia if a predetermined portion of said sensed evens occur within said tachycardia window.

12. The method of claim 11, wherein said predetermined portion is six out of a seven last sensed events.

13. An apparatus for treating a tachyarrhythmia of the heart comprising:

detection means for detecting a tachyarrhythmia;

shock means for delivering a shock to the heart;

reconfirmation means for confirming a presence of the tachyarrhythmia subsequent to detection by said detection means and for reconfirming the presence of the tachyarrhythmia immediately prior to delivery of said shock means, said reconfirmation means controlling said shock means so that only if the presence of said tachyarrhythmia is both confirmed and reconfirmed does said shock means deliver said shock to the heart, said shock means including:

an energy storage means;

a discharge means for discharging to the heart energy stored in said storage means; and means for supplying energy to said energy storage means;

said apparatus further comprising:

monitoring means for monitoring a value of energy supplied to said energy storage means; and comparison means for comparing said value to a predetermined value, said comparison means being for controlling said reconfirmation means to reconfirm the presence of the tachyarrhythmia when said value of energy supplied to said energy storage means reaches said predetermined value.

14. An apparatus for treating a tachyarrhythmia of the heart comprising:

detection means for detecting a tachyarrhythmia;

shock means for delivering a shock to the heart; and reconfirmation means for confirming a presence of the tachyarrhythmia subsequent to detection by said detection means and for reconfirming the presence of the tachyarrhythmia immediately prior to delivery of a shock by said shock means, said reconfirmation means controlling said shock means so that only if the presence of the tachyarrhythmia is both confirmed and reconfirmed does said shock means deliver said shock to the heart, said detection means continuously detecting for said tachyarrhythmia and continuously providing an output indicative of detection thereof, and said reconfirmation means being responsive to said continuously provided output to determine whether a tachyarrhythmia is still present.

* * * * *